United States Patent
Kato et al.

(10) Patent No.: US 6,630,341 B2
(45) Date of Patent: Oct. 7, 2003

(54) PHOSPHOHEXULOISOMERASE AND GENE THEREFOR

(75) Inventors: Nobuo Kato, Kameoka (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/897,956

(22) Filed: Jul. 5, 2001

(65) Prior Publication Data

US 2002/0061578 A1 May 23, 2002

(30) Foreign Application Priority Data

Jul. 7, 2000 (JP) ........................................ 2000-206799

(51) Int. Cl.$^7$ .............................. C12N 9/90; C12N 15/61
(52) U.S. Cl. .................... 435/233; 435/252.3; 536/23.2
(58) Field of Search .............................. 435/233, 252.3; 576/23.2

(56) References Cited

U.S. PATENT DOCUMENTS 6,331,428 B1   12/2001   Kato ........................... 435/233

FOREIGN PATENT DOCUMENTS

| JP | 11-127869 | * | 5/1999 |
| JP | 2000-41683 | | 2/2000 |

OTHER PUBLICATIONS

R. Mitsui, et al., Journal of Bacteriology, vol. 182, No. 4, pp. 944–948, "A Novel Operon Encoding Formaldehyde Fixation: The Ribulose Monophosphate Pathway in the Gram-–Positive Facultative Methylotropic Bacterium Mycobacterium Gastri MB19", Feb. 2000.

H. Yasueda, et al., Journal of Bacteriology, vol. 181, No. 23, pp. 7154–7160, "Bacillus Subtilis yckG and yckF Encode Two Key Enzymes of the Ribulose Monophosphate Pathway used by Methylotrophs, and yckH is Required for Their Expression", Dec. 1999.

N. Arfman, et al., Methods in Enzymology, vol. 188, pp. 391–397, "3–Hexulose–6–Phosphate Synthase from Thermotolerant Methylotroph Bacillus C1", 1990.

N. Arfman, et al., Archives of Microbiology, vol. 152, No. 3, pp. 280–288, "Methanol Metabolism in Thermotolerant Methylotrophic Bacillus Strains Involving a Novel Catabolic Nad–Dependent Methanol Dehydrogenase as a Key Enzyme", 1989.

N. Kato, et al., Agric. Biol. Chem., vol. 41, No. 7, pp. 1133–1140, "Properties of 3–Hexulose Phosphate Synthase and Phospho–3–Hexuloisomerase of a Methanol–Utilizing Bacterium, 77a", 1977.

T. Ferenci, et al., Biochem. J., vol. 144, pp. 477–486, "Purification and Properties of 3–Hexulose Phosphate Synthase and Phospho–3–Hexuloisomerase from Methylococcus Capsulatus", 1974.

* cited by examiner

*Primary Examiner*—Charles L. Patterson, Jr.
(74) *Attorney, Agent, or Firm*—Oblon, Spivak, McClelland, Maier & Neustadt, P.C.

(57) ABSTRACT

There are provided a DNA coding for phosphohexuloisomerase, which is a protein defined in the following (A) or (B), and a method for producing the enzyme:

(A) a protein having the amino acid sequence of SEQ ID NO: 3 shown in Sequence Listing, (B) a protein having the amino acid sequence of SEQ ID NO: 3 shown in Sequence Listing including substitution, deletion, insertion or addition of one or several amino acid residues and having phosphohexulose isomerase activity.

12 Claims, No Drawings

PHOSPHOHEXULOISOMERASE AND GENE THEREFOR

BACKGROUND OF THE INVENTION

1. Field of the Invention

The present invention relates to phosphohexuloisomerase and a DNA coding for it. More precisely, the present invention related to phosphohexuloisomerase derived from a thermotolerant bacterium, *Bacillus brevis*, and a DNA coding for it.

2. Description of the Related Art

Among organisms that can utilize single carbon (C1) compounds such as methane and methanol as a carbon source (methylotrophs), there are known those having the ribulose monophosphate (RuMP) pathway as a pathway for metabolizing such compounds. Important key enzymes of this pathway are hexulose phosphate synthase (HPS, 3-hexulose-6-phosphate synthase), which catalyzes the initial reaction of the ribulose monophosphate pathway, and phosphohexuloisomerase (PHI, phospho-3-hexuloisomerase), which catalyzes the subsequent reaction.

By the way, biochemical substances in which specific position of a target compound molecule is labeled with a stable isotope, carbon 13 ($^{13}C$), are useful for study of biological metabolic pathway. Furthermore, it has recently become a very important technique to investigate behaviors of metabolic products in living bodies by using carbon 13-NMR techniques in diagnosis of various diseases and daily health examination. For such novel techniques, it is necessary and desired to provide compounds labeled at a certain target position with carbon 13 at a low cost.

As one of systems for producing such target compounds as mentioned above, a method can be conceived, in which a series of enzymes are prepared for synthesizing labeled D-fructose 6-phosphate using labeled formaldehyde and ribulose 5-phosphate, and a target labeled compound is efficiently prepared in a reaction system utilizing the enzymes. Hexulose phosphate synthase, which is an enzyme initially acts in the reaction system, has been isolated from several kinds of microorganisms, and some of its characteristics have been elucidated. Such microorganisms include, for example, *Methylomonas capsulatus* (J. R. Quayle, *Methods in Enzymology*, 188, p.314, 1990), Methylomonas M15 strain (*Methods in Enzymology*, 188, p.319, 1990), *Methylomonas aminofaciens* 77a strain (*Biochim. Biophys. Acta.*, 523, p.236, 1978), *Mycobacterium gastri* MB19 (*Methods in Enzymology*, 188, p.393, 1990), and *Acetobacter methanolicus* MB58 (*Methods in Enzymology*, 188, p.401, 1990).

Further, as for phosphohexuloisomerase, it has been partially purified from *Methylomonas aminofaciens* 77a strain (Agric. Biol. Chem., 41 (7), p1133, 1977), and a purified enzyme and a gene coding for it were isolated from a gram-positive facultative methanol assimilating bacterium, *Mycobacterium gastri* (Japanese Patent Laid-open Publication (Kokai) No. 11-127869).

Enzymes and proteins produced by thermotolerant bacteria are generally stable at a high temperature, and most of them are also stable against pH variation and organic solvents. Therefore, applications thereof have been highly developed as diagnostic agents, industrial catalysts and so forth. As a C1 metabolic system enzyme of thermotolerant methanol assimilating bacteria, only hexulose phosphate synthase has been purified from *Bacillus methanolicus* C1 strain (*Methods in Enzymology*, 188, p.393, 1990), and its detailed structure and gene therefor are unknown. On the other hand, as for phosphohexuloisomerase of thermotolerant bacteria, not only the structure of enzyme protein and gene therefor, but also purification of the enzyme have not been reported.

SUMMARY OF THE INVENTION

The inventors of the present invention found that, in the course of cloning of a gene coding for hexulose phosphate synthase (henceforth also referred to as "hps") of *Bacillus brevis* S1 strain, a gene coding for PHI (henceforth also referred to as "phi") existed in the DNA fragment containing hps. And they isolated the phi gene, introduced this gene into an *Escherichia coli* cell, and examined activity of the expression product to confirm that the gene coded for PHI. Thus, they accomplished the present invention.

That is, the present invention provides the followings.

(1) A DNA coding for a protein defined in the following (A) or (B):

(A) a protein having the amino acid sequence of SEQ ID NO: 3 shown in Sequence Listing, (B) a protein having the amino acid sequence of SEQ ID NO: 3 shown in Sequence Listing including substitution, deletion, insertion or addition of one or several amino acid residues and having phosphohexulose isomerase activity.

(2) The DNA according to (1), which is a DNA defined in the following (a) or (b):

(a) a DNA containing a nucleotide sequence consisting of at least the residues of nucleotide numbers 1149–1700 of the nucleotide sequence of SEQ ID NO: 1 shown in Sequence Listing, (b) a DNA which is hybridizable with a nucleotide sequence consisting of at least the residues of nucleotide numbers 1149–1700 of the nucleotide sequence of SEQ ID NO: 12 shown in Sequence Listing under a stringent condition, and codes for a protein having phosphohexulose isomerase activity.

(3) A cell into which a DNA according to (1) or (2) is introduced in such a manner that phosphohexulose isomerase encoded by the DNA can be expressed.

(4) A method for producing phosphohexulose isomerase, comprising culturing the cell according to (3) in a medium to produce and accumulate phosphohexulose isomerase in culture, and collecting the phosphohexulose isomerase from the culture.

(5) A protein defined in the following (A) or (B):

(A) a protein having the amino acid sequence of SEQ ID NO: 3 shown in Sequence Listing, (B) a protein having the amino acid sequence of SEQ ID NO: 3 shown in Sequence Listing including substitution, deletion, insertion or addition of one or several amino acid residues and having phosphohexulose isomerase activity.

According to the present invention, a DNA coding for phosphohexuloisomerase is obtained, and this enables efficient production of that enzyme. As a result, it becomes possible to provide labeled substances that are important and required for medicine or biochemical basic research in large quantities at low cost.

PREFERRED EMBODIMENTS OF THE INVENTION

Hereafter, the present invention will be explained in detail.

<1> DNA of the Present Invention

The DNA of the present invention was found in the DNA fragment containing hps gene of *Bacillus brevis* S1 strain adjacent to and downstream from the hps gene, and it can be isolated and obtained from chromosomal DNA of *Bacillus brevis*. Specifically, as shown in the examples described later, the DNA of the present invention was obtained from chromosomal DNA of *Bacillus brevis* as follows.

First, HPS is purified from *Bacillus brevis*. As the *Bacillus brevis*, the *Bacillus brevis* S1 strain can be mentioned. This strain is subcultured at NCIMB (The National Collections of Industrial and Marine Bacteria) with the accession number of NCIMB12524.

HPS can be purified from cell free extract of the S1 strain by Q-Sepharose column chromatography, Buthyl-Toyopearl column chromatography and Superdex 200 column chromatography to such a degree that it can be detected as a single band in SDS-PAGE. In each purification step, HPS activity can be measured by the method described in *Methods in Enzymology*, vol. 188, 397–401 (1990).

A partial amino acid sequence of the purified HPS is determined, and oligonucleotide primers for PCR (polymerase chain reaction) are synthesized based on the obtained amino acid sequence information. Then, PCR is performed by using genomic DNA prepared from the *Bacillus brevis* S1 strain as a template. The genomic DNA can be obtained by the method of Saito et al. (described in *Biochim. Biophys. Acta,* 72, 619–629 (1963)). If the oligonucleotides having the nucleotide sequences of SEQ ID NOS: 7 and 8 shown in Sequence Listing are used as primers, a DNA fragment of about 400 bp will be obtained by the above PCR.

Then, based on the nucleotide sequence of the hps fragment obtained as described above, a DNA fragment containing the hps gene in its full length is obtained from *Bacillus brevis* S1 strain chromosomal DNA by, for example, the inverted PCR method (Genetics, vol. 120, pp.621–623, 1988) using oligonucleotides having the nucleotide sequences of SEQ ID NOS: 9 and 10 as primers.

At first, the inventors of the present invention attempted to screen a genomic library of *Bacillus brevis* S1 strain by using the aforementioned hps fragment of about 400 bps as a probe. However, although the possible cause was unknown, probably because a problem resided in the ligation of the chromosomal DNA fragment to the vector, colonies having a number of genomic libraries sufficient for the screening could not be formed, and thus they had to give up use of the ordinary method.

Therefore, they attempted the cloning by the inverted PCR technique as described above, and successfully obtained a DNA fragment containing the hps gene. The result of nucleotide sequence determination for about 1.8 kb in the clone fragment in a length of about 3 kb obtained as described above is shown in Sequence Listing as SEQ ID NO: 1. In this region, two open reading frames (orfs) were contained. The amino acid sequences encoded by each orf are shown in SEQ ID NOS: 2 and 3 from the 5' end side. Since the first orf among these completely coincided to a partial amino acid sequence of HPS, it was demonstrated to be hps. On the other hand, the second orf was confirmed to be phi, i.e., the DNA of the present invention, by investigating the activity of a protein obtained by expressing this orf.

When homology searching was performed for the nucleotide sequence of phi and the amino acid sequence encoded thereby by using commercially available software (GENETYX), they showed 65.6% of homology on the nucleotide level and 64.3% of homology on the amino acid level to ykcF of *Bacillus subtillis*. The homology was calculated as a ratio of the number of exactly the same amino acid residues in yckF and phi to the total number of amino acid residues encoded by yckF.

As described above, while the DNA of the present invention was discovered by chance in connection with the purification of HPS and isolation of hps, the DNA of the present invention was obtained by expressing the second orf and confirming the activity of the expressed product based on a conception that the second orf should code for phi.

The DNA of the present invention was obtained as described above. However, since its nucleotide sequence and the amino acid sequence encoded thereby were elucidated by the present invention, the DNA of the present invention can then be obtained from a genomic DNA library of a thermotolerant bacterium belonging to the genus Bacillus, for example, *Bacillus brevis* S1 strain, by hybridization utilizing an oligonucleotide produced based on the nucleotide sequence or amino acid sequence as a probe. The DNA of the present invention can also be obtained by performing PCR utilizing the aforementioned oligonucleotide as a primer and genomic DNA of a thermotolerant bacterium belonging to the genus Bacillus as a template.

Methods for construction of genomic DNA library, hybridization, PCR, preparation of plasmid DNA, digestion and ligation of DNA, transformation and so forth are described in by Sambrook, J., Fritsch, E. F., Maniatis, T., Molecular Cloning, Cold Spring Harbor Laboratory Press, 1.21 (1989).

The *Escherichia coli* JM109/pKPS1 harboring a plasmid pKPS1 containing the DNA of the present invention and expressing PHI under control of tac promoter, which was obtained in the examples mentioned later and given a private number of AJ13707, was deposited on Jul. 5, 2000 at the National Institute of Bioscience and Human Technology of Agency of Industrial Science and Technology (currently, the independent administrative corporation, National Institute of Advanced Industrial Science and Technology, International Patent Organism Depositary)(Chuo Dai-6, 1-1 Higashi 1-Chome, Tsukuba-shi, Ibaraki-ken, Japan, postal code: 305-5466) as the accession number of FERM P-17952, and transferred from the original deposit to international deposit based on Budapest Treaty on Jun. 25, 2001, and has been deposited as the accession number of FERM BP-7639.

The DNA of the present invention may code for PHI including substitution, deletion, insertion or addition of one or several amino acid residues at one or a plurality of positions, provided that the activity of encoded PHI is not deteriorated. The number of "several" amino acid residues differs depending on positions or types of amino acid residues in the three-dimensional structure of the protein. However, the encoded PHI may be one showing homology of 65% or more, preferably 80% or more, to the total amino acid sequence constituting PHI and having the PHI activity. Specifically, the number of "several" amino acid residues is preferably 2–60, more preferably 2–30, further preferably 2–10.

A DNA coding for substantially the same protein as PHI described above can be obtained by, for example, modifying the nucleotide sequence by, for example, the site-directed mutagenesis method so that the amino acid sequence should involve substitution, deletion, insertion or addition of one or more amino acid residues at a specified site. Such a DNA modified as described above may also be obtained by a conventionally known mutation treatment. The mutation treatment includes a method of treating DNA coding for PHI in vitro, for example, with hydroxylamine, and a method for treating a microorganism, for example, a bacterium belonging to the genus Escherichia, harboring a DNA coding for PHI with ultraviolet irradiation or a mutating agent usually used for mutation treatment such as N-methyl-N'-nitro-N-nitrosoguanidine (NTG) and nitrous acid.

The substitution, deletion, insertion, addition or inversion of nucleotide as described above also includes a naturally occurring mutant or variant on the basis of, for example, individual difference or difference in species or genus of microorganisms that harbor phi.

A DNA coding for substantially the same protein as PHI described above can be obtained by expressing such a DNA having a mutation as described above in a suitable cell, and examining the PHI activity of the expression product. A DNA coding for substantially the same protein as PHI can also be obtained by isolating a DNA hybridizable with a DNA having, for example, the nucleotide sequence corresponding to nucleotide numbers of 1149–1700 of the nucleotide sequence shown in SEQ ID NO: 1 or a probe that can be prepared from the nucleotide sequence under a stringent condition, and coding for a protein having the PHI activity from a DNA coding for PHI including a mutation or a cell harboring it. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 70% are hybridized with each other, and DNA's having homology lower than the above level are not hybridized with each other. Alternatively, the stringent condition is exemplified by a condition under which DNA's are hybridized with each other at a salt concentration corresponding to an ordinary condition of washing in Southern hybridization, i.e., 1×SSC, 0.1% SDS, preferably 0.1×SSC, 0.1% SDS, at 60° C.

As the probe, a partial sequence of the phi gene can also be used. Such a probe can be produced by PCR (polymerase chain reaction) using oligonucleotides produced based on the nucleotide sequence of each gene as primers and a DNA fragment containing each gene as a template. When a DNA fragment in a length of about 300 bp is used as the probe, the washing condition for the hybridization may consists of 50° C., 2×SSC and 0.1% SDS.

Genes hybridizable under such a condition as described above include those having a stop codon generated in a coding region of the genes, and those having no activity due to mutation of active center. However, such mutants can be readily removed by ligating each of the genes with a commercially available activity expression vector, and measuring the PHI activity by the method described above.

<2> Production of Hexulose Phosphate Isomerase

PHI can be produced by allowing expression of the aforementioned DNA of the present invention using a suitable host-vector system.

As the host for the expression of the phi gene, there can be mentioned various prokaryote cells including *Escherichia coli* and various eucaryote cells including *Saccharomyces cerevisiae*, animal cells and plant cells. Among these, prokaryote cells, especially *Escherichia coil* cells, are preferred.

As the vector for introducing the phi gene into the aforementioned host, there can be mentioned, for example, pUC19, pUC18, pBR322, pHSG299, pHSG298, pHSG399, pHSG398, RSF1010, pMW119, pMW118, pMW219, pMW218 and so forth. Other than these, a vector of phage DNA can also be used. The phi gene can be introduced into the host by transforming the host with a recombinant vector obtained by ligating the phi gene to any one of those vectors. The phi gene may also be introduced into genome of the host by a method using transduction, transposon (Berg, D. E. and Berg C. M., *Bio/Technol.*, 1, 417 (1983)), Mu phage (Japanese Patent Laid-open Publication No. 2-109985/1990) or homologous recombination (Experiments in Molecular Genetics, Cold Spring Harbor Lab. (1972)).

Further, in order to obtain efficient expression of the phi gene, a promoter functioning in the host cell such as lac, trp and $P_L$ may be ligated to the DNA sequence coding for PHI in its upstream region. If a vector containing a promoter is used as the vector, the ligation of the phi gene, vector and promoter can be performed at once. As such a vector, pKK 223-3 containing tac promoter (Pharmacia) can be mentioned.

For the transformation, there can be used, for example, a method of treating recipient cells with calcium chloride so as to increase the permeability for DNA, which has been reported for *Escherichia coli* K-12 (Mandel, M. and Higa, A., *J. Mol. Biol.*, 53, 159 (1970)); and a method of preparing competent cells from cells which are at the growth phase followed by introducing the DNA thereinto, which has been reported for *Bacillus subtilis* (Duncan, C. H., Wilson, G. A. and Young, F. E., *Gene*, 1, 153 (1977)). In addition to these, also employable is a method of making DNA-recipient cells into protoplasts or spheroplasts, which can easily take up recombinant DNA, followed by introducing the recombinant DNA into the cells, which method is known to be applicable to Bacillus subtilis, actinomycetes and yeasts (Chang, S. and Choen, S. N., Molec. Gen. Genet., 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Sci. USA*, 75, 1929 (1978)). The method for transformation may be suitably selected from these methods depending on the cells used as the host.

Although the phi gene may be any one so long as it shows the PHI activity when it is expressed, it is preferably a gene containing a DNA coding for the amino acid sequence of SEQ ID NO: 3 shown in Sequence Listing, or a DNA containing the nucleotide residues of the nucleotide numbers 1149–1700 in the nucleotide sequences of SEQ ID NO: 1 shown in of Sequence Listing. Further, as mentioned above, it may be one containing a DNA coding for PHI including substitution, deletion, insertion, addition or inversion of one or several amino acid residues at one or a plurality of positions, so long as the activity of the encoded PHI is not deteriorated.

PHI can be produced by culturing a cell introduced with the phi gene as described above in a medium to produce and accumulated PHI in culture, and collecting PHI from the culture. The medium used for the culture can be suitably selected depending on a host to be used. When *Escherichia coli* is used as the host and phi is expressed with the aid of tac promoter, if the host is cultured in a medium such as LB medium at 37° C., IPTG (isopropyl-â-D-thiogalactopyranoside), which is an inducer for the tac promoter, is added at a final concentration of 0.5 mM several hours after the start of the culture, and the culture is further continued, PHI is accumulated in the cells. When extracellular secretion of PHI is allowed by using a suitable secretion system, PHI is accumulated in the medium.

PHI produced as described above can be purified from cell extract or medium by using usual purification methods for enzymes such as ion exchange chromatography, gel filtration chromatography, adsorption chromatography and solvent precipitation as required.

PHI obtained by the present invention can be used for producing [1-$^{13}$C] D-glucose 6-phosphate from methanol labeled with carbon 13. The preparation of this [1-$^{13}$C] D-glucose 6-phosphate can be performed as follows, for example. Methanol is oxidized into formaldehyde by using alcohol oxidase prepared from methanol assimilating yeast, *Candida boidinii*. The obtained formaldehyde is condensed with ribulose 5-phosphate through aldol condensation by the action of HPS to form arabino-3-hexulose 6-phosphate. In this case, since ribulose 5-phosphate is unstable, ribose 5-phosphate is isomerized into ribulose 5-phosphate by the action of phosphoriboisomerase in the same reaction system for use in the HPS reaction. The arabino-3-hexulose 6-phosphate produced in the aforementioned reaction is converted into fructose 6-phosphate by the action of PHI, which is further converted into glucose 6-phosphate by the action of glucose 6-phosphate isomerase. Because the PHI content is markedly lower than the HPS content in general, it is difficult to utilize PHI for the aforementioned reaction in most of cases. Further, it is considered that the reaction can be continued for a long period of time by using PHI of a thermotolerant bacterium. Since phi of a thermotolerant bacterium was isolated and a method for efficiently producing PHI was provided by the present invention, it became possible to stably perform the aforementioned reaction for practical use.

BEST MODE FOR CARRYING OUT THE INVENTION

Hereafter, the present invention will be explained more specifically with reference to the following examples.

First, the method for measurement of HPS activity (*Methods in Enzymology*, vol. 188, 397–401 (1990)) used in the examples will be explained.

[Method for Measurement of HPS Activity]

To 0.15 ml of water, 0.05 ml each of the following Solutions A to E were added and mixed in a cuvette (d=1.0 cm), and preliminarily heated at 30° C. for about 3 minutes. To the cuvette, 0.1 ml of 10 mM formaldehyde solution was added to start the reaction. The reaction was allowed at 30° C. for 5 minutes, and then 0.1 ml of 0.5 N hydrochloric acid was added to the mixture to stop the reaction. The reaction mixture was diluted 20 times and added with 2 ml of Nash reagent (described in *Biochem. J.*, 55, 416, 1953), and decrease of formaldehyde in the reaction mixture was measured. In a control experiment, water was used instead of the ribose 5-phosphate solution.

[Reagents]

A: 500 mM Potassium phosphate buffer, pH 7.5
B: 50 mM Magnesium chloride aqueous solution
C: 50 mM Ribose 5-phosphate aqueous solution
D: 100 U/ml of phosphoriboisomerase solution
E: Enzyme preparation (50 mM phosphate buffer (pH 7.5) containing 1 mM DTT)

EXAMPLE 1

Purification of Hexulose Phosphate Synthase (HPS) Produced by *Bacillus brevis* S1 Strain First, for purification of HPS, *Bacillus brevis* S1 strain (NCIMB 12524) was added to 11 of 2 L-volume flasks each containing 500 ml of Medium A having the following composition, and cultured at 45° C. for 16 hours with shaking.

| [Composition of Medium A] | |
|---|---|
| Methanol | 2 ml/L |
| Dipotassium hydrogenphosphate | 4.65 g/L |
| Sodium hydrogenphosphate monohydrate | 1.5 g/L |
| Ammonium sulfate | 1.5 g/L |
| Magnesium sulfate heptahydrate | 0.2 g/L |
| Yeast extract | 0.5 g/L |
| Peptone | 0.5 g/L |
| Casamino Acid | 0.5 g/L |
| Vitamin Solution *1 | 1 ml/L |
| Trace metal solution *2 | 0.2 ml/L |
| (pH 7) | |

*1: In 100 ml, 10 mg of pantothenic acid, 10 mg of riboflavin, 1 mg of vitamin $B_{12}$, 1 mg of lipoic acid, 1 mg of folic acid, 10 mg of biotin, 10 mg of thiamine, 10 mg of nicotinamide, 2 mg of p-aminobenzoic acid and 10 mg of pyridoxal phosphate were contained.
*2: In 100 ml, 0.55 g of $CaCl_2$ 2H2O, 0.51 g of $MnCl_2$ $4H_2O$, 2.2 g of $ZnSO_4$ $7H_2O$, 0.16 g of $CuSO_4$ $5H_2O$, 0.50 g of $FeSO_4$ $7H_2O$, 0.16 g of $CoCl_2$ $6H_2O$, 0.011 g of $(NH_4)Mo_7O_{24}$ $4H_2O$ and 5.0 g of EDTA (ethylenediamine tetraacetate) were contained.

After the culture, the cells were collected to obtain about 11.3 g of cells. The cells were suspended in 106 ml of 50 mM Tris-HCl buffer (pH 7.5) containing 1 mM DTT, and disrupted by sonication. The disrupted cell suspension was centrifuged at 12000 rpm for 20 minutes at 4° C., and the supernatant was used as cell free extract. Then, this supernatant was dialyzed overnight against 20 mM Tris-HCl buffer (pH 7.5) containing 1 mM DTT, 0.15 mM PMSF (phenylmethanesulfonyl fluoride) and 5 MM $MgCl_2$, applied to a Q-Sepharose column (Pharmacia) equilibrated with the same buffer, and eluted with a linear gradient of from 0 M to 0.5 M of potassium chloride to obtain a fraction showing the activity of HPS (16 ml). By this purification step, HPS was purified by about 2.9 times.

Then, the aforementioned fraction was added with solid ammonium sulfate to a concentration of 1.7 M with stirring, and centrifuged at 8000 rpm for 10 minutes, and the supernatant was collected. Further, the supernatant was passed through a filter having a pore size of 0.22 μm to remove microparticles, and applied to a Buthyl-Toyopearl (TOSOH CORP.) column equilibrated with 50 mM Tris-HCl buffer (pH 7.0) containing 1 mM DTT, 0.15 mM PMSF and 5 mM $MgCl_2$, and eluted with a linear gradient of from 1.7 M to 0 M of ammonium sulfate (elution rate: 2 ml/minute). In this way, a fraction showing high HPS activity was obtained (12 ml).

Subsequently, the above fraction was concentrated to a volume of 2 ml in Centriprep (Millipore Co.), then applied to a Superdex 200 (Pharmacia) column equilibrated with 100 mM Tris-HCl buffer (pH 7.5) containing 1 mM DTT, 0.15 mM PMSF and 5 mM $MgCl_2$, and eluted with the same buffer (elution rate: 2 ml/minute) to obtain a fraction showing high activity. By these purification steps, the target HPS could be purified.

Homogeneity of the enzyme was confirmed by the fact that, when the purified specimen was subjected SDS-PAGE on 15% polyacrylamide gel, the protein was detected as a substantially single band. The molecular weight determined by this SDS-PAGE was about 25000.

EXAMPLE 2

Partial Structure of Hexulose Phosphate Synthase (HPS) Produced by *Bacillus brevis* S1 Strain Subsequently, a partial amino acid sequence of HPS obtained in Example 1 was determined. The protein band of HPS developed by SDS-PAGE was blotted on a PVDF (polyvinylidene fluoride) membrane in a conventional manner, and the band was excised. Then, the N-terminus amino acid sequence of the protein was analyzed by the Edman degradation method. As a result, it was found to be MQLQLALDLVNIEEAKQVVAEVQEYVDIVE (SEQ ID NO: 4). Further, as for the internal amino acid sequence of the protein, the protein was partially degraded with V8 protease, subjected to SDS-PAGE, and similarly blotted on a PVDF membrane. Then, all of the bands of peptide fragments that could be detected were excised, and the amino acid sequences thereof were analyzed by the Edman degradation method. As a result, VAKAAEHGADIVTI-LAAAEDVSIKGAVEEAKKLGXK (SEQ ID NO: 5) and MGVDYIXVHAGYDLQAVGKN (SEQ ID NO: 6) were determined.

EXAMPLE 3

Acquisition of Genomic DNA of *Bacillus brevis* S1 Strain

The *Bacillus brevis* S1 strain was inoculated into 5 ml of Medium B (CM129 medium (OXOID LTD.)), and cultured overnight at 45° C. This culture was inoculated into 500 ml of Medium B at a ratio of 1% and cultured until OD (610 nm) reached about 1.0, and then the culture broth was centrifuged to collect the cells. The cells were washed with saline-EDTA solution (composition: 0.15 M NaCl, 0.01 M EDTA, pH 8.0), and then suspended in 500 ml of the same solution, and the suspension was added with 80 mg lysozyme and kept at 37° C. for 3 hours.

Then, the suspension was added with 2 ml of 25% SDS and 10 ml of protease K (10 mg/ml), and shaken overnight at 37° C. On the following day, the suspension was treated at 60° C. for 20 minutes, added with 14 ml of 5 M sodium perchlorate and 30 ml of chloroform/isoamyl alcohol mixture (mixing ratio: 24:1), and gently stirred for 30 minutes. This suspension was centrifuged at 20° C. for 30 minutes at 3000 rpm, and the aqueous layer was collected, added with 30 ml of phenol/chloroform mixture, and gently stirred for 30 minutes. Then, it was centrifuged again at 20° C. for 30 minutes at 3000 rpm and the aqueous layer was collected.

The above supernatant was added with a 2-fold amount of cold ethanol, and DNA was collected by winding it around a Pasteur pipette. The DNA was washed with 70% ethanol, air-dried, and then dissolved in 5 ml of TE solution (10 mM Tris-HCl buffer containing 1 mM EDTA (pH 7.5)). Subsequently, the solution was added with 50 ml of 10 mg/ml RNase and allowed to react at 37° C. for 30 minutes. The solution was added with 30 ml of 0.1× SSC solution and treated with phenol/chloroform. The aqueous layer was collected and added with 0.5-fold amount of cold isopropanol. The DNA was collected by winding it around a Pasteur pipette, washed with 70% ethanol, air-dried, and dissolved in 10 ml of TE solution to obtain a genomic DNA fragment (concentration: 0.12 µg/µl).

EXAMPLE 4

Cloning of Partial Sequence of Hexulose Phosphate Synthase Gene hps of *Bacillus brevis* S1 Strain by PCR Based on the amino acid sequence elucidated in Example 2, a mixed nucleotide primer for an N-terminus region, HPS-BaN2 (5'-GARGTNCARGARTAYGTNGAYATHGTNGA-3', SEQ ID NO: 7), and a mixed nucleotide primer for an internal region of the protein, HPS-BaI3 (5'-TTYTTNCCNACNGCYTGNARRTCRTA-3', SEQ ID NO: 8), were synthesized in a conventional manner. Then, PCR was performed by using the genomic DNA prepared in Example 3 as a template and the DNA primers, HPS-BaN2 and HPS-BaI3 (25 cycles each consisting of reactions at 95° C. for 1 minute, 52° C. for 1 minute and 72° C. for 3 minutes were performed).

The reaction mixture was subjected to agarose gel electrophoresis to purify the DNA fragment amplified by PCR (about 400 bp). Then, this was ligated to pT7Blue by using Ligation Kit ver. II (Takara Shuzo), and the *E. coli* DH5alα strain was transformed with the ligation solution to obtain transformants. One of plasmids harbored by them was designated as pTHS1. The nucleotide sequence of the inserted DNA fragment portion of pTHS1 was determined in a conventional manner, and it was found to have a length of 376 bp and highly homologous to sequences of other methylotrophs containing hps in homology search using BLAST Search.

EXAMPLE 5

Cloning of Hexulose Phosphate Synthase Gene hps of *Bacillus brevis* S1 Strain and Discovery of Presence of phi Gene First, existing position of the hps gene on the genome was examined by the Southern analysis. The genome prepared as described above was digested with various restriction enzymes, subjected to electrophoresis, and blotted on a nylon membrane according to the method of Southern (*Journal of Molecular Biology*, 98, p.503, 1975). As a probe, a DNA fragment containing a part of the hps gene in a length of about 400 bp was used, which was separated from pTHS1 containing a part of hps produced in Example 4 digested with restriction enzymes BamHI and SpeI by electrophoresis on 2% agarose gel.

The membrane on which DNA was immobilized was pre-hybridized in a conventional manner, then added with a labeled probe, and allowed to hybridize overnight at 55° C. The probe was labeled by using Alk. Phos. DIRECT reagent (Amersham). The membrane was washed at 55° C. twice with each of first and second washing solutions, and the label of the probe was exposed to an X-ray film. As a result, the products obtained by digesting the genomic DNA with EcoRI, BamHI and SalI formed a single band at positions of 6.0 kb, 5.5 kb and 3.0 kb, respectively.

Based on the above results, it was attempted to produce a plasmid library by ligating the genome of S1 strain digested with BamHI or SalI to vector pUC19 digested with the same restriction enzyme. However, a large number of *E. coli* cells transformed by the ligated plasmid could not be obtained by this method. Thus, the target hps gene could not be obtained by a usual cloning method.

Therefore, the inventors of the present invention decided to clone the target gene by the inverted PCR method (*Genetics*, vol. 120, p.621–623, 1988). For use in the inverted PCR, a primer for a region from an internal position in HPS to the N-terminus side, hps-ivB1 (5'-TAACCGGAGTACCGATTTCC-3', SEQ ID NO: 9), and a primer for a region from an internal position in HPS to the C-terminus side, hps-ivS1 (5'-CACGTGGATACGATCTCCA-3', SEQ ID NO: 10), were synthesized based on the nucleotide sequence of the hps fragment.

On the other hand, an about 3 kbp fragment containing upstream and downstream regions of hps gene was obtained by the inverted PCR method using the genomic DNA digested with SalI and then self-ligated as a template. As for the PCR conditions, a cycle consisting of reactions at 95° C. for 1 minute, 56° C. for 1 minute and 72° C. for 3 minutes was repeated for 25 cycles. The PCR product was purified by electrophoresis and ligated to the pGEM-T vector (Promega). The E. Coli DH5α strain was transformed with the ligation solution. Plasmids were collected from the transformants, and their structures were confirmed to obtain the target PGHS1.

Then, pGHS1 was subcloned in order to investigate the structures around the hps gene. First, pGHS1 was digested with a restriction enzyme SalI, and two DNA fragments (about 2 kb and about 4 kb) were separated by agarose gel electrophoresis. The smaller DNA fragment was digested with SalI, and ligated to pBluescriptII SK+ (Stratagene) treated with CIAP to produce pGHS1-HN. On the other hand, the larger fragment of 4 kbp was self-ligated, and used for transformation of E. coli to obtain a plasmid pGHS1-HC. By using these plasmids, the nucleotide sequences of the sequence portions inserted into the vectors were determined. As a result, it was confirmed that the upstream and downstream regions of hps existed in the fragment of about 3 kb obtained by the aforementioned inverted PCR, and thus the structures around hps were elucidated. The sequence is shown in SEQ ID NO: 1.

A partial amino acid sequence of the enzymatic protein determined in Example 2 was found in the amino acid sequence deduced from the nucleotide sequence of the DNA fragment obtained as described above, and it was found that this gene exactly coded for HPS. This amino acid sequence is shown in SEQ ID NO: 2.

On the other hand, the inventors of the present invention noticed that another open reading frame (abbreviated as "orf") existed downstream from the aforementioned hps gene. Known sequences were searched for those homologous to the amino acid sequence (SEQ ID NO: 3) deduced from the sequence of the orf. As a result, it showed 64% of homology to the yckF gene of Bacillus subtilis, which was confirmed to code for PHI (Journal of Bacteriology, vol. 181, p.7154, 1999)). Therefore, it was attempted to confirm if this orf coded for PHI or not by expressing this gene.

EXAMPLE 6

Expression of Novel Phosphohexuloisomerase Gene phi of Bacillus brevis S1 Strain in Escherichia coli The phi gene was obtained by PCR from the genomic DNA of Bacillus brevis S1 strain (NCIMB12524). A 5' end primer PHI-ESDN (5'-GGAATTCCTAAGGAGGTTTTTATATGATGCAGACA ACTGAATTC-3', SEQ ID NO: 11) and a 3' end primer PHI-EcC1 (5'-GGAATTCCCTACTCGAGATTGGCATGTCT-3', SEQ ID NO: 12) were synthesized in a conventional manner. After heat denaturation treatment of DNA at 95° C. for 5 minutes, PCR was performed by using genomic DNA of Bacillus brevis S1 strain as a template, the above primers and ExTaq-DNA polymerase (Takara Shuzo) in a conventional manner (cycle of reactions at 950C for 1 minute, 56° C. for 1 minute and 72° C. for 2 minutes was repeated for 30 cycles, and then the system was kept at 72° C. for 3 minutes). Thus, a DNA fragment containing the phi gene was obtained.

Then, the aforementioned DNA fragment was introduced into PGEM-T easy vector (Promega) to produce pGPS1.

Further, this pGPS1 was digested with a restriction enzyme NotI, and the digested ends were blunt-ended by using T4-DNA polymerase to obtain a phi gene fragment having blunt ends. On the other hand, an expression vector pKK 223-3 (Pharmacia) was digested with a restriction enzyme SmaI. The phi gene fragment and the vector fragment were ligated by using DNA ligase to produce the target plasmid pKPS1 that contained the phi gene under control of a promoter on the vector. Escherichia coli JM109 was transformed with this pKPS1 in a conventional manner to obtain a transformant JM109/pKPS1. This strain designated as AJ13707 was deposited on Jul. 5, 2000 at the National Institute of Bioscience and Human Technology of Agency of Industrial Science and Technology (currently, the independent administrative corporation, National Institute of Advanced Industrial Science and Technology, International Patent Organism Depositary)(Chuo Dai-6, 1-1 Higashi 1-Chome, Tsukuba-shi, Ibaraki-ken, Japan, postal code: 305-5466) as the accession number of FERM P-17952, and transferred from the original deposit to international deposit based on Budapest Treaty on Jun. 25, 2001, and has been deposited as the accession number of FERM BP-7639.

The AJ13707 strain was grown overnight at 37° C. on LB agar medium containing ampicillin (50 μg/ml), and the emerged colonies were inoculated into 5 ml of LB liquid medium similarly containing ampicillin. Culture was started at 37° C. After 4–5 hours, 0.5 mM IPTG (isopropyl-â-D-thiogalactopyranoside) was added to the culture to induce transcription from tac promoter existing on pKPS1. Further, after culturing for 14 hours, 3 ml of the culture broth was centrifuged to collect the cells. These cells were washed twice with 50 mM potassium phosphate buffer (pH 7.5) and then suspended in 100 μl of the same buffer containing 1 mM DTT (dithiothreitol). Then, the cells were disrupted by loading the cell suspension on a beat beater, the disrupted cell suspension was centrifuged (15000 rpm, 40 minutes), and the supernatant was used as crude cell extract.

EXAMPLE 7

Activity Measurement of Product of phi Gene of Bacillus brevis S1 Strain

Detection of PHI activity was performed by using the crude cell extract obtained in Example 6. As the activity measurement method, formaldehyde assimilation was measured as eventual reduction of oxidized nicotinamide adenine dinucleotide phosphate by glucose-6-phosphate dehydrogenase.

The following reagents were mixed as described below to prepare reagent solutions. One milliliter of Solution A, 0.5 ml of Solution B, 0.5 ml of Solution C and 1 ml of Solution D were mixed to prepare 3 ml of a reaction buffer. On the other hand, 1 ml each of Solutions G, H, I and J were mixed to prepare an enzyme solution in a total volume of 4 ml.
(Reagents)
A: 1 M Potassium phosphate buffer, pH 7.5
B: 100 mM NADP Aqueous solution
C: 100 mM Magnesium chloride aqueous solution
D: 50 mM Ribose 5-phosphate aqueous solution
E: Enzyme preparation (50 mM phosphate buffer solution containing 1 mM DTT, pH 7.5)
F: 50 mM Formaldehyde aqueous solution
G: 100 U/ml of phosphoriboisomerase (PRI)
H: 100 U/ml of phosphoglucoisomerase (PGI)
I: 100 U/ml of glucose 6-phosphate dehydrogenase (G6PDH)
J: 100 U/ml of purified HPS (Methods Enzymol., 188, p.397–401, 1990)

In an amount of 0.15 ml of the aforementioned reaction buffer and 0.20 ml of the enzyme solution were added to 0.55 ml of water, put into a cuvette (d=1.0 cm), further added with 0.05 ml of the aforementioned enzyme preparation E, stirred and preliminarily heated at 30° C. for 2 minutes. The mixture was added with 0.05 ml of Solution F and mixed sufficiently, and increase of absorbance of the mixture at 340 nm was measured by using a spectrophotometer with a blank of wafer. From the initial linear segment of the absorbance curve, absorbance change per 1 minute was obtained (this value is represented as "Atest"). As a blank test, the same procedure as described above was performed except that 0.05 ml of a diluted enzyme solution was added instead of the enzyme preparation to obtain absorbance change per 1 minute (this value is represented as "Ablank").

One unit of the enzyme activity was calculated as an amount of enzyme reducing 1 μmol of NADP into NADPH per 1 minute in accordance with the following equation.

$$\text{PHI activity (Unit}/ml) = (\Delta test - \Delta blank) \times D \times V/6.22 \times L$$

D: Dilution ratio of enzyme
V: Amount of reaction mixture (1 ml in this case)
L: Amount of enzyme preparation in reaction mixture (0.05 ml in this case)

Molecular extinction coefficient of NADPH (30 $nm$)=6.22×10³ $M^-cm^{-1}$

As a result, while PHI activity could not be detected in the crude extract prepared from *Escherichia coli* JM109 harboring the vector pKK 223-3 which did not carry the phi gene, high PHI activity (187 Unit/mg protein) was found in the crude cell extract prepared from the *Escherichia coli* harboring pKPS1 (AJ13707). This demonstrated that the gene obtained by the inventors of the present invention coded for PHI.

What is claimed is:

1. A DNA coding for a protein defined in the following (A) or (B):
   (A) a protein having the amino acid sequence of SEQ ID NO: 3,
   (B) a protein having the amino acid sequence of SEQ ID NO: 3 including substitution, deletion, insertion or addition of one or several amino acid residues wherein said protein is at least 80% homologous to the sequence of SEQ ID NO: 3 and has phosphohexulose isomerase activity.

2. The DNA according to claim 1, which is a DNA defined in the following (a) or (b):
   (a) a DNA having a nucleotide sequence consisting of at least the residues of nucleotide numbers 1149–1700 of the nucleotide sequence of SEQ ID NO: 1,
   (b) a DNA which is hybridizable to the complement of a nucleotide sequence consisting of at least the residues of nucleotide numbers 1149–1700 of the nucleotide sequence of SEQ ID NO: 1 under a stringent condition, and codes for a protein having phosphohexulose isomerase activity.

3. A cell comprising the DNA according to claim 1, wherein said protein having phosphohexulose isomerase activity can be expressed.

4. A method for producing phosphohexulose isomerase, comprising culturing the cell according to claim 3 in a medium to produce and accumulate phosphohexulose isomerase in the culture, and collecting the phosphohexulose isomerase from the culture.

5. The DNA according to claim 1, wherein said DNA codes for a protein having the amino acid sequence of SEQ ID NO: 3 including substitution, deletion, insertion or addition of one or several amino acid residues wherein said protein is at least 80% homologous to the sequence of SEQ ID NO: 3 and has phosphohexulose isomerase activity.

6. A cell comprising the DNA according to claim 2, wherein said protein having phosphohexulose isomerase activity can be expressed.

7. A method for producing phosphohexulose isomerase, comprising the steps of culturing the cell according to claim 6 in a medium to produce and accumulate phosphohexulose isomerase in the culture, and collecting the phosphohexulose isomerase from the culture.

8. A DNA coding for a protein having the amino acid sequence of SEQ ID NO: 3 including substitution, deletion, insertion or addition of 2 to 60 amino acid residues and has phosphohexulose isomerase activity.

9. The DNA according to claim 8, wherein said DNA codes for a protein having the amino acid sequence of SEQ ID NO: 3 including substitution, deletion, insertion or addition of 2 to 30 amino acid residues and has phosphohexulose isomerase activity.

10. The DNA according to claim 8, wherein said DNA codes for a protein having the amino acid sequence of SEQ ID NO: 3 including substitution, deletion, insertion or addition of 2 to 10 amino acid residues and has phosphohexulose isomerase activity.

11. A cell comprising the DNA according to claim 8, wherein said protein having phosphohexulose isomerase activity can be expressed.

12. A method for producing phosphohexulose isomerase, comprising culturing the cell according to claim 11 in a medium to produce and accumulate phosphohexulose isomerase in the culture, and collecting the phosphohexulose isomerase from the culture.

* * * * *

SEQUENCE LISTING

<160> NUMBER OF SEQ ID NOS: 12

<210> SEQ ID NO 1
<211> LENGTH: 1823
<212> TYPE: DNA
<213> ORGANISM: Bacillus brevis
<220> FEATURE:
<221> NAME/KEY: CDS
<222> LOCATION: (508)..(1140)
<223> OTHER INFORMATION:
<221> NAME/KEY: CDS
<222> LOCATION: (1149)..(1700)
<223> OTHER INFORMATION:

<400> SEQUENCE: 1

```
agccaatgac ggaaaatgat tgaggcattt tttgatccag aaataaatta tacaaagcag        60
gatagatttt ccttttagct aaatcccctg tcgcgccaaa caagacaaag gtcatcgaat       120
ccacttttca tacctccaca ttaacatttg ttgcggcaaa tattagtata atatgtatat       180
tttttatatg taagtacgca cttattaatc ttatagttac aaatttatat aaagtataaa       240
taatatacta taaaaaatct tatggaaagt gatggatcat tcatacctt ttttcccgta        300 ttgtttacat tttctatagg aatttttct taatagtata cttttatac tatgtgttaa         360 taaagtgcgt acttttaaa aaatttgata gatagtatat taacagtgta caggcaaaag       420
aaggaataca cacatttgct tgtacaatac aaagttacat aattgtaaca aaaaaaacta       480
aaaattttga aaaggagtgt ataattt atg caa ctt caa tta gct cta gat ttg       534
                                 Met Gln Leu Gln Leu Ala Leu Asp Leu
                                  1               5 gta aac att gaa gaa gca aaa caa gta gta gct gag gtt cag gag tat         582
Val Asn Ile Glu Glu Ala Lys Gln Val Val Ala Glu Val Gln Glu Tyr
 10              15                  20                  25 gtc gat atc gta gaa atc ggt act ccg gtt att aaa att tgg ggt ctt         630
Val Asp Ile Val Glu Ile Gly Thr Pro Val Ile Lys Ile Trp Gly Leu
                 30                  35                  40 caa gct gta aaa gaa gtt aaa gac gca ttc cct cat tta caa gtt tta         678
Gln Ala Val Lys Glu Val Lys Asp Ala Phe Pro His Leu Gln Val Leu
             45                  50                  55 gct gac atg aaa act atg gat gct gca gca tat gaa gtt gct aaa gca         726
Ala Asp Met Lys Thr Met Asp Ala Ala Ala Tyr Glu Val Ala Lys Ala
             60                  65                  70
```

```
                                    -continued gct gag cat ggc gct gat atc gta aca att ctt gca gca gct gaa gat        774
Ala Glu His Gly Ala Asp Ile Val Thr Ile Leu Ala Ala Ala Glu Asp
     75                  80                  85 gta tca att aag ggt gct gta gaa gaa gcg aaa aaa ctt ggc aaa aaa        822
Val Ser Ile Lys Gly Ala Val Glu Glu Ala Lys Lys Leu Gly Lys Lys
 90                  95                 100                 105 atc ctt gtt gac atg atc gca gtt aaa aat tta gaa gag cgt gca aaa        870
Ile Leu Val Asp Met Ile Ala Val Lys Asn Leu Glu Glu Arg Ala Lys
                     110                 115                 120 caa gtg gat gaa atg ggt gta gac tac att tgt gtt cac gct gga tac        918
Gln Val Asp Glu Met Gly Val Asp Tyr Ile Cys Val His Ala Gly Tyr
            125                 130                 135 gat ctc caa gca gta ggt aaa aac cca tta gat gat ctt aag aga att        966
Asp Leu Gln Ala Val Gly Lys Asn Pro Leu Asp Asp Leu Lys Arg Ile
        140                 145                 150 aaa gct gtc gtg aaa aat gca aaa act gct att gca ggc gga atc aaa       1014
Lys Ala Val Val Lys Asn Ala Lys Thr Ala Ile Ala Gly Gly Ile Lys
    155                 160                 165 tta gaa aca ttg cct gaa gtt atc aaa gca gaa ccg gat ctt gtc att       1062
Leu Glu Thr Leu Pro Glu Val Ile Lys Ala Glu Pro Asp Leu Val Ile
170                 175                 180                 185 gtc ggc ggc ggt att gct aac caa act gat aaa aaa gca gca gct gaa       1110
Val Gly Gly Gly Ile Ala Asn Gln Thr Asp Lys Lys Ala Ala Ala Glu
                    190                 195                 200 aaa ata aat aaa tta gtt aaa caa ggg tta tgatcagc atg cag aca act      1160
Lys Ile Asn Lys Leu Val Lys Gln Gly Leu             Met Gln Thr Thr
            205                 210                         215 gaa ttc tta tct gaa atc gta aaa gaa tta agt aat tcg gtt aac caa       1208
Glu Phe Leu Ser Glu Ile Val Lys Glu Leu Ser Asn Ser Val Asn Gln
        220                 225                 230 atc gcc gat gaa gaa gcg gaa gca ctg gta aac gga att ctt caa tca       1256
Ile Ala Asp Glu Glu Ala Glu Ala Leu Val Asn Gly Ile Leu Gln Ser
    235                 240                 245 aag aaa gta ttt gtt gcc ggt gca gga aga tcc ggt ttt atg gca aaa       1304
Lys Lys Val Phe Val Ala Gly Ala Gly Arg Ser Gly Phe Met Ala Lys
250                 255                 260 tcc ttt gcg atg cgc atg atg cac atg gga att gat gcc tat gtc gtt       1352
Ser Phe Ala Met Arg Met Met His Met Gly Ile Asp Ala Tyr Val Val
        265                 270                 275 ggc gaa acc gta act cct aac tat gaa aaa gaa gac att tta att att       1400
Gly Glu Thr Val Thr Pro Asn Tyr Glu Lys Glu Asp Ile Leu Ile Ile
280                 285                 290                 295 gga tcc ggc tct gga gaa aca aaa ggt ctc gtt tcc atg gct caa aaa       1448
Gly Ser Gly Ser Gly Glu Thr Lys Gly Leu Val Ser Met Ala Gln Lys
                    300                 305                 310 gca aaa agc ata ggt gga acc att gcg gct gta acg att aat cct gaa       1496
Ala Lys Ser Ile Gly Gly Thr Ile Ala Ala Val Thr Ile Asn Pro Glu
            315                 320                 325 tca aca atc gga caa tta gcg gat atc gtt att aaa atg cca ggt tcg       1544
Ser Thr Ile Gly Gln Leu Ala Asp Ile Val Ile Lys Met Pro Gly Ser
        330                 335                 340 cct aaa gat aaa tca gaa gca agg gaa act att caa cca atg gga tcc       1592
Pro Lys Asp Lys Ser Glu Ala Arg Glu Thr Ile Gln Pro Met Gly Ser
    345                 350                 355 ctt ttc gag caa aca tta tta tta ttc tat gat gct gtc att ttg aga       1640
Leu Phe Glu Gln Thr Leu Leu Leu Phe Tyr Asp Ala Val Ile Leu Arg
360                 365                 370                 375 ttc atg gag aaa aaa ggc ttg gat aca aaa aca atg tac gga aga cat       1688
Phe Met Glu Lys Lys Gly Leu Asp Thr Lys Thr Met Tyr Gly Arg His
                    380                 385                 390
```

```
gcc aat ctc gag taggcgtgga attaagaaaa ggaagaccgc gatgctttgc      1740
Ala Asn Leu Glu
        395 ggtctttcct tgttttttt acattacatg atgtttatat agtgtcgacc atatgggaga  1800 gctcccaacg cgttggatgc ata                                         1823
```

<210> SEQ ID NO 2
<211> LENGTH: 211
<212> TYPE: PRT
<213> ORGANISM: Bacillus brevis

<400> SEQUENCE: 2

```
Met Gln Leu Gln Leu Ala Leu Asp Leu Val Asn Ile Glu Glu Ala Lys
1               5                   10                  15

Gln Val Val Ala Glu Val Gln Glu Tyr Val Asp Ile Val Glu Ile Gly
            20                  25                  30

Thr Pro Val Ile Lys Ile Trp Gly Leu Gln Ala Val Lys Glu Val Lys
        35                  40                  45

Asp Ala Phe Pro His Leu Gln Val Leu Ala Asp Met Lys Thr Met Asp
    50                  55                  60

Ala Ala Ala Tyr Glu Val Ala Lys Ala Ala Glu His Gly Ala Asp Ile
65                  70                  75                  80

Val Thr Ile Leu Ala Ala Ala Glu Asp Val Ser Ile Lys Gly Ala Val
                85                  90                  95

Glu Glu Ala Lys Lys Leu Gly Lys Lys Ile Leu Val Asp Met Ile Ala
            100                 105                 110

Val Lys Asn Leu Glu Glu Arg Ala Lys Gln Val Asp Glu Met Gly Val
        115                 120                 125

Asp Tyr Ile Cys Val His Ala Gly Tyr Asp Leu Gln Ala Val Gly Lys
    130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Gly Ile Ala Asn
            180                 185                 190

Gln Thr Asp Lys Lys Ala Ala Ala Glu Lys Ile Asn Lys Leu Val Lys
        195                 200                 205

Gln Gly Leu
    210
```

<210> SEQ ID NO 3
<211> LENGTH: 184
<212> TYPE: PRT
<213> ORGANISM: Bacillus brevis

<400> SEQUENCE: 3

```
Met Gln Thr Thr Glu Phe Leu Ser Glu Ile Val Lys Glu Leu Ser Asn
1               5                   10                  15

Ser Val Asn Gln Ile Ala Asp Glu Glu Ala Glu Ala Leu Val Asn Gly
            20                  25                  30

Ile Leu Gln Ser Lys Lys Val Phe Val Ala Gly Ala Gly Arg Ser Gly
        35                  40                  45

Phe Met Ala Lys Ser Phe Ala Met Arg Met Met His Met Gly Ile Asp
    50                  55                  60
```

```
Ala Tyr Val Val Gly Glu Thr Val Thr Pro Asn Tyr Glu Lys Glu Asp
 65                  70                  75                  80

Ile Leu Ile Ile Gly Ser Gly Ser Gly Glu Thr Lys Gly Leu Val Ser
                 85                  90                  95

Met Ala Gln Lys Ala Lys Ser Ile Gly Gly Thr Ile Ala Ala Val Thr
            100                 105                 110

Ile Asn Pro Glu Ser Thr Ile Gly Gln Leu Ala Asp Ile Val Ile Lys
        115                 120                 125

Met Pro Gly Ser Pro Lys Asp Lys Ser Glu Ala Arg Glu Thr Ile Gln
    130                 135                 140

Pro Met Gly Ser Leu Phe Glu Gln Thr Leu Leu Leu Phe Tyr Asp Ala
145                 150                 155                 160

Val Ile Leu Arg Phe Met Glu Lys Lys Gly Leu Asp Thr Lys Thr Met
                165                 170                 175

Tyr Gly Arg His Ala Asn Leu Glu
            180
```

<210> SEQ ID NO 4
<211> LENGTH: 30
<212> TYPE: PRT
<213> ORGANISM: Bacillus brevis

<400> SEQUENCE: 4

```
Met Gln Leu Gln Leu Ala Leu Asp Leu Val Asn Ile Glu Glu Ala Lys
 1               5                  10                  15

Gln Val Val Ala Glu Val Gln Glu Tyr Val Asp Ile Val Glu
            20                  25                  30
```

<210> SEQ ID NO 5
<211> LENGTH: 36
<212> TYPE: PRT
<213> ORGANISM: Bacillus brevis
<220> FEATURE:
<221> NAME/KEY: MISC_FEATURE
<222> LOCATION: (35)..(35)
<223> OTHER INFORMATION: Xaa=unknown amino acid

<400> SEQUENCE: 5

```
Val Ala Lys Ala Ala Glu His Gly Ala Asp Ile Val Thr Ile Leu Ala
 1               5                  10                  15

Ala Ala Glu Asp Val Ser Ile Lys Gly Ala Val Glu Glu Ala Lys Lys
            20                  25                  30

Leu Gly Xaa Lys
         35
```

<210> SEQ ID NO 6
<211> LENGTH: 20
<212> TYPE: PRT
<213> ORGANISM: Bacillus brevis
<220> FEATURE:
<221> NAME/KEY: MISC_FEATURE
<222> LOCATION: (7)..(7)
<223> OTHER INFORMATION: Xaa=unknown amino acid

<400> SEQUENCE: 6

```
Met Gly Val Asp Tyr Ile Xaa Val His Ala Gly Tyr Asp Leu Gln Ala
 1               5                  10                  15

Val Gly Lys Asn
            20
```

<210> SEQ ID NO 7

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (6)..(6)
<223> OTHER INFORMATION: y = t/u or c
<221> NAME/KEY: misc_feature
<222> LOCATION: (18)..(18)
<223> OTHER INFORMATION: y = t/u or c
<221> NAME/KEY: misc_feature
<222> LOCATION: (27)..(27)
<223> OTHER INFORMATION: h = a or c or t/u

<400> SEQUENCE: 7
gargtncarg artaygtnga yathgtnga                                29

<210> SEQ ID NO 8
<211> LENGTH: 26
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (3)..(3)
<223> OTHER INFORMATION: y = t/u or c
<221> NAME/KEY: misc_feature
<222> LOCATION: (6)..(6)
<223> OTHER INFORMATION: n = any nucleotide
<221> NAME/KEY: misc_feature
<222> LOCATION: (9)..(9)
<223> OTHER INFORMATION: n = any nucleotide
<221> NAME/KEY: misc_feature
<222> LOCATION: (12)..(12)
<223> OTHER INFORMATION: n = any nucleotide
<221> NAME/KEY: misc_feature
<222> LOCATION: (15)..(15)
<223> OTHER INFORMATION: y = t/u or c
<221> NAME/KEY: misc_feature
<222> LOCATION: (18)..(18)
<223> OTHER INFORMATION: n= any nucleotide
<221> NAME/KEY: misc_feature
<222> LOCATION: (20)..(20)
<223> OTHER INFORMATION: r = g or a
<221> NAME/KEY: misc_feature
<222> LOCATION: (21)..(21)
<223> OTHER INFORMATION: r = g or a
<221> NAME/KEY: misc_feature
<222> LOCATION: (24)..(24)
<223> OTHER INFORMATION: r = g or a

<400> SEQUENCE: 8
ttyttnccna cngcytgnar rtcrta                                   26

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
taaccggagt accgatttcc                                          20

<210> SEQ ID NO 10
<211> LENGTH: 19
<212> TYPE: DNA
<213> ORGANISM: Artificial Sequence
<220> FEATURE:
<223> OTHER INFORMATION: Synthetic DNA

<400> SEQUENCE: 10

-continued

```
cacgtggata cgatctcca                                            19

<210> SEQ ID NO 11
<211> LENGTH: 44
<212> TYPE: DNA
<213> ORGANISM: Artificial Sequence
<220> FEATURE:
<223> OTHER INFORMATION: Synthetic DNA

<400> SEQUENCE: 11
ggaattccta aggaggtttt tatatgatgc agacaactga attc                 44

<210> SEQ ID NO 12
<211> LENGTH: 29
<212> TYPE: DNA
<213> ORGANISM: Artificial Sequence
<220> FEATURE:
<223> OTHER INFORMATION: Synthetic DNA

<400> SEQUENCE: 12
ggaattccct actcgagatt ggcatgtct                                  29
```